United States Patent
Meyer

(10) Patent No.: US 6,584,353 B2
(45) Date of Patent: Jun. 24, 2003

(54) OPERATING METHOD FOR AN IMPLANTABLE CARDIOLOGIC DEVICE, IN PARTICULAR A HEART PACEMAKER

(75) Inventor: Wolfgang Meyer, Erlangen (DE)

(73) Assignee: Biotronik Mess- und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 206 days.

(21) Appl. No.: 09/729,854

(22) Filed: Dec. 6, 2000

(65) Prior Publication Data

US 2001/0003160 A1 Jun. 7, 2001

(30) Foreign Application Priority Data

Dec. 6, 1999 (DE) .......................... 199 58 735

(51) Int. Cl.⁷ .............................................. A61N 1/365
(52) U.S. Cl. ........................... 607/27; 607/17; 600/547
(58) Field of Search ............................. 607/19, 17, 18, 607/20, 24, 27; 600/547

(56) References Cited

U.S. PATENT DOCUMENTS 6,308,098 B1 * 10/2001 Meyer .................. 600/547

* cited by examiner

Primary Examiner—Jeffrey R. Jastrzab
(74) Attorney, Agent, or Firm—Browdy and Neimark, P.L.L.C.

(57) ABSTRACT

An operating method for an implantable cardiologic device comprises the following steps for detection of a significant event or condition a patient is subject to:
- measurement of intracardiac impedance;
- detection of the morphologic signal course of the impedance, based on at least two morphologically representative parameters of the signal course;
- continuous storage of the parameter data from a defined measuring period;
- computation of a correlation coefficient for the stored parameter data; and
- comparison of the correlation coefficient with a reference correlation coefficient, with transgression of a defined deviation of the correlation coefficient from the reference correlation coefficient indicating the presence of a significant event.

14 Claims, 5 Drawing Sheets

| Pat. Nr. | 1 | 2 | 3 | 4 | 5 | 6 | 7 | 8 |
|---|---|---|---|---|---|---|---|---|
| 1 | 1 | 0,95366 | 0,98465 | 0,97275 | 0,98035 | 0,98776 | 0,97361 | 0,97143 |
| 2 | 0,95366 | 1 | 0,97431 | 0,9836 | 0,87811 | 0,95125 | 0,98914 | 0,97625 |
| 3 | 0,98465 | 0,97431 | 1 | 0,99458 | 0,94699 | 0,97704 | 0,99304 | 0,99737 |
| 4 | 0,97275 | 0,9836 | 0,99458 | 1 | 0,92302 | 0,97762 | 0,99104 | 0,99723 |
| 5 | 0,98035 | 0,87811 | 0,94699 | 0,92302 | 1 | 0,96636 | 0,92025 | 0,9274 |
| 6 | 0,98776 | 0,95125 | 0,97704 | 0,97762 | 0,96636 | 1 | 0,96371 | 0,97048 |
| 7 | 0,97361 | 0,98914 | 0,99304 | 0,99104 | 0,92025 | 0,96371 | 1 | 0,99277 |
| 8 | 0,97143 | 0,97625 | 0,99737 | 0,99723 | 0,9274 | 0,97048 | 0,99277 | 1 |
| 1 | 1 | 0,98893 | 0,98966 | 0,98052 | 0,99421 | 0,98455 | 0,98364 | 0,97933 |
| 2 | 0,98893 | 1 | 0,97835 | 0,99414 | 0,96888 | 0,97954 | 0,98173 | 0,98313 |
| 3 | 0,98966 | 0,97835 | 1 | 0,97895 | 0,98763 | 0,98766 | 0,99526 | 0,9931 |
| 4 | 0,98052 | 0,99414 | 0,97895 | 1 | 0,95902 | 0,9811 | 0,98576 | 0,99017 |
| 5 | 0,99421 | 0,96888 | 0,98763 | 0,95902 | 1 | 0,98054 | 0,97453 | 0,96775 |
| 6 | 0,98455 | 0,97954 | 0,98766 | 0,9811 | 0,98054 | 1 | 0,97789 | 0,98386 |
| 7 | 0,98364 | 0,98173 | 0,99526 | 0,98576 | 0,97453 | 0,97789 | 1 | 0,99664 |
| 8 | 0,97933 | 0,98313 | 0,9931 | 0,99017 | 0,96775 | 0,98386 | 0,99664 | 1 |
| 1 | 1 | 0,99014 | 0,99401 | 0,99074 | 0,9908 | 0,97477 | 0,97724 | 0,98451 |
| 2 | 0,99014 | 1 | 0,97871 | 0,99629 | 0,9662 | 0,97093 | 0,98756 | 0,98304 |
| 3 | 0,99401 | 0,97871 | 1 | 0,97518 | 0,98628 | 0,97659 | 0,97856 | 0,98874 |
| 4 | 0,99074 | 0,99629 | 0,97518 | 1 | 0,96861 | 0,97218 | 0,98208 | 0,97895 |
| 5 | 0,9908 | 0,9662 | 0,98628 | 0,96861 | 1 | 0,94586 | 0,94527 | 0,95893 |
| 6 | 0,97477 | 0,97093 | 0,97659 | 0,97218 | 0,94586 | 1 | 0,98409 | 0,99476 |
| 7 | 0,97724 | 0,98756 | 0,97856 | 0,98208 | 0,94527 | 0,98409 | 1 | 0,99431 |
| 8 | 0,98451 | 0,98304 | 0,98874 | 0,97895 | 0,95893 | 0,99476 | 0,99431 | 1 |

Rows 1–8: total; rows 9–16: day; rows 17–24: night.

FIG.4

| | Pat. Nr. | 1 | 2 | 3 | 4 | 5 | 6 | 7 | 8 |
|---|---|---|---|---|---|---|---|---|---|
| total | 1 | 1 | 0,9543 | 0,98455 | 0,94487 | 0,90201 | 0,94908 | 0,88467 | 0,94714 |
| | 2 | 0,9543 | 1 | 0,97276 | 0,95977 | 0,76655 | 0,99188 | 0,95757 | 0,97374 |
| | 3 | 0,98455 | 0,97276 | 1 | 0,98406 | 0,8614 | 0,98274 | 0,94067 | 0,98759 |
| | 4 | 0,94487 | 0,95977 | 0,98406 | 1 | 0,83526 | 0,98369 | 0,93841 | 0,99561 |
| | 5 | 0,90201 | 0,76655 | 0,8614 | 0,83526 | 1 | 0,77517 | 0,64051 | 0,80093 |
| | 6 | 0,94908 | 0,99188 | 0,98274 | 0,98369 | 0,77517 | 1 | 0,97086 | 0,99364 |
| | 7 | 0,88467 | 0,95757 | 0,94067 | 0,93841 | 0,64051 | 0,97086 | 1 | 0,96483 |
| | 8 | 0,94714 | 0,97374 | 0,98759 | 0,99561 | 0,80093 | 0,99364 | 0,96483 | 1 |
| day | 1 | 1 | 0,9804 | 0,9874 | 0,9801 | 0,97983 | 0,95291 | 0,91351 | 0,95088 |
| | 2 | 0,9804 | 1 | 0,98026 | 0,99522 | 0,94442 | 0,98835 | 0,94964 | 0,98192 |
| | 3 | 0,9874 | 0,98026 | 1 | 0,98414 | 0,9797 | 0,97059 | 0,92386 | 0,97767 |
| | 4 | 0,9801 | 0,99522 | 0,98414 | 1 | 0,93925 | 0,99194 | 0,96909 | 0,9861 |
| | 5 | 0,97983 | 0,94442 | 0,9797 | 0,93925 | 1 | 0,91033 | 0,83856 | 0,92185 |
| | 6 | 0,95291 | 0,98835 | 0,97059 | 0,99194 | 0,91033 | 1 | 0,96937 | 0,99635 |
| | 7 | 0,91351 | 0,94964 | 0,92386 | 0,96909 | 0,83856 | 0,96937 | 1 | 0,95493 |
| | 8 | 0,95088 | 0,98192 | 0,97767 | 0,9861 | 0,92185 | 0,99635 | 0,95493 | 1 |
| night | 1 | 1 | 0,99305 | 0,98681 | 0,9924 | 0,99472 | 0,92811 | 0,91369 | 0,96393 |
| | 2 | 0,99305 | 1 | 0,98033 | 0,99629 | 0,98093 | 0,95541 | 0,93929 | 0,97618 |
| | 3 | 0,98681 | 0,98033 | 1 | 0,98611 | 0,98796 | 0,94191 | 0,91507 | 0,98344 |
| | 4 | 0,9924 | 0,99629 | 0,98611 | 1 | 0,97977 | 0,96332 | 0,94539 | 0,98267 |
| | 5 | 0,99472 | 0,98093 | 0,98796 | 0,97977 | 1 | 0,90132 | 0,8815 | 0,95241 |
| | 6 | 0,92811 | 0,95541 | 0,94191 | 0,96332 | 0,90132 | 1 | 0,98298 | 0,98357 |
| | 7 | 0,91369 | 0,93929 | 0,91507 | 0,94539 | 0,8815 | 0,98298 | 1 | 0,95199 |
| | 8 | 0,96393 | 0,97618 | 0,98344 | 0,98267 | 0,95241 | 0,98357 | 0,95199 | 1 |

FIG. 5

OPERATING METHOD FOR AN IMPLANTABLE CARDIOLOGIC DEVICE, IN PARTICULAR A HEART PACEMAKER

BACKGROUND OF THE INVENTION

1. Field of the Invention

The invention relates to an operating method for an implantable cardiologic device, in particular a heart pacemaker, for detection of a significant event or condition a patient is exposed to, such as a change from day to night, a pathologic condition or the like.

2. Background Art

As for the background of the invention, clinical studies in connection with heart pacemakers examined the unipolar intracardiac impedance for possible conclusions to be drawn from the measured results as to a possible improvement of the possibilities of control of heart pacemakers. Subject of these examinations was a heart pacemaker which transmitted corresponding impedance data to an external monitor. On the occasion of two after-care examinations taking place six and twelve weeks after implantation of the pacemaker, data on the signal course of the measured intracardiac impedance were detected and stored over a period of 24 hours. From this measurement of the intracardiac impedance, the morphologic signal course of the impedance was detected so that the impedance curve of the heart during a heartbeat could be recorded. As explained below in conjunction with the exemplary embodiment, collective features and differences of the measured impedance curves were analyzed by statistical methods during the two after-care examinations. The idea was to make use of the results obtained for further optimization of the heart pacemaker functions, for instance in connection with day/night adaptation of the control parameters or for recognition of pathologic irregularities such as susceptibility to extrasystoles or sudden cardiac death.

The clinical studies have for example shown that the morphology of the averaged unipolar intracardiac impedance is comparatively stable for the period of the after-care examinations. Statistical evaluations have found differences between various patients in the correlation of the measured values; these differences can be exploited for diagnostic purposes. Finally, differences between the average day and night curves offer a criterion for simple day/night differentiation and recognition.

SUMMARY OF THE INVENTION

Proceeding from this, the invention proposes an operating method for an implantable cardiologic device, in particular for a heart pacemaker, having certain method steps for detection of a significant event or condition a patient is exposed to. In this regard, the invention does not involve complete control of a heart pacemaker, but the partial aspect defined in the purpose specified. Within the scope of a certain control program being implemented on a heart pacemaker, a corresponding function can be allotted to this partial aspect, this function being fulfilled by the operating method according to the invention.

This operating method comprises the following method steps:

measurement of intracardiac impedance;

detection of the morphologic signal course of the impedance based on at least one morphologically representative parameter of the signal course;

continuous storage of the parameter of a defined measuring period;

computation of a correlation coefficient for the stored parameter; and comparison of the correlation coefficient with a reference correlation coefficient, with transgression of a defined deviation of the correlation-coefficient from a reference correlation coefficient indicating the presence of the significant event.

The method bases on the measurement of the intracardiac impedance of the heart and detects the morphologic signal course of the impedance by an as a rule unipolar electrode that is anchored in the myocardium, which means measurement not only of a certain value, but of the impedance in dependence on various instants during a cycle of cardiac contraction. In the extreme, one parameter and preferably two morphologically representative parameter data of the signal course, such as the peak-to-peak amplitude can be sufficient as parameter data. These parameter data are then detected over a defined measuring period which may take several hours of the day, depending on the storing capacity of the implantable cardiologic device. Correlation coefficients are computed for these stored parameter data, to which end varying computing methods may be used, depending on the function and design of the operating method. In this regard, "correlation coefficient" does not exclusively mean the computation of a correlation along strictly statistical lines. It is to imply generally the determination of expressive values such as the computation of the square deviation, standard deviation, autocorrelation, the virtual correlation strictly speaking, the cross correlation, or even simply the deviation of a signal course from a standard or reference signal course. This will be explained in detail below.

For the purposes of the invention, the correlation coefficients are compared with a reference correlation coefficient, the presence of a significant event being indicated whenever a defined deviation between these two correlation coefficients is exceeded.

In accordance with further preferred embodiments of the method, the various correlation coefficients can be continuously computed and compared with the reference correlation coefficients. This means continuous monitoring of the heart for any possible deviations from standard, it being possible, for evaluation purposes, continuously to store preferably the correlation coefficients computed during a certain interval. On the whole, what takes place is an evaluation of the parameter data of the signal course, accessing a certain window of time which, during operation of the implantable cardiologic device, extends backwards from the respective current time by the duration of the evaluation interval.

During operation of the implantable cardiologic device, the mentioned evaluation methods may for instance be employed to recognize a change from day to night or from night to day. If for instance autocorrelation coefficients are continuously computed and evaluated by comparison of parameter data that differ by a defined time lag, a change from day to night (or vice versa) will occasion a decrease of the autocorrelation coefficient as a result of the accompanying change of the typical signal course; after passage of the change through the interval, the autocorrelation coefficient rises again to its initial value. The change generates a minimum in the chronological order of the autocorrelation coefficients, which is recognized and may be used for instance for adjustment of the operating program of the implantable cardiologic device from day operation to night operation.

According to another preferred embodiment of the operating method according to the invention, any possible pathologic conditions of the heart can be recognized by the determined correlation coefficients being analyzed and by the transgression of a defined deviation from reference correlation coefficients being recognized as the presence of a possibly pathologic condition. Correspondingly, the implantable cardiologic device may set a warning signal which is detectable from outside.

Since competent clinical examinations have shown that the correlation coefficients may change significantly in dependence on the time for which the implant has been implanted, it is of advantage to make the reference correlation coefficients adjustable in dependence on the duration of implantation of the implant. Thus, the operating method that takes place in the implanted device is optimally adjusted to the action time thereof.

A special embodiment of the operating method according to the invention aims at the statistic and spectral analysis of the parameter data of the signal course of the average intracardiac impedance. As a correlation coefficient for the stored parameters, it will do to detect the deviation of the individual signal courses—for instance the square or standard deviation—from an averaged signal course or from each other and to analyze same by means of spectral analysis. This analysis proceeds from detecting deviations of comparatively small frequencies that repeat themselves regularly and are coupled with physiologic functions of the body in a manner still to be explained. Based on this detection, the operating method may implement corresponding actions in the cardiac pacemaker, which adjust themselves to the detected situation.

According to another preferred embodiment, the operating method according to the invention can be designed for the possibility of selection between varying evaluation methods and parameters as indicated in the foregoing claims. This selection may take place automatically in dependence on the preceding result of evaluation by corresponding implementation of the operating program. Even a purely preset selection by the operating program is conceivable without any reference to the prior results of evaluation.

The following is a detailed explanation of the scientific findings underlying the invention and the operating method based thereon concerning a cardiac pacemaker in its varying forms, taken in conjunction with the drawing.

BRIEF DESCRIPTION OF THE DRAWING

FIG. 4 is a table of the cross correlation data between the mean value overall curve, the mean value curve of the day and the mean value curve of the night of various patients at a point of time of six weeks after implantation of a heart pacemaker;

FIG. 5 is a table analogous to FIG. 4 of the cross correlation data, three months after implantation of the pacemaker;

DESCRIPTION OF THE PREFERRED EMBODIMENT

The clinical study underlying the invention bases on the after-care examination of eight patients carried out six weeks and three months, respectively, after implantation of the cardiac pacemaker. By the aid of a unipolar electrode, the intracardiac impedance was performed for 24 hours, using a heart pacemaker of Applicant of the type "INOS". The pacemaker was programmed to the DDD mode. The measurement curves determined by the electrode were detected by a "Unilyzer-Holter monitor". Each signal curve during a heartbeat was recorded and stored in a manner dissolved into 32 measuring points. During these measurements, a rough day/night differentiation was performed, based on a very rough approach toward night recognition by the aid of the circadian variation of a coefficient of variability of the intracardiac impedance signal.

Proceeding from this, in the measurements performed, all signal curves of the patients were averaged over the entire day, over only the hours of the day and over only the hours of the night, and the average morphologic signal course was determined by the aid of the local standard deviation at each measuring point of all the curves, and the correlation of the varying pairs of curves was determined.

In detail, the following was determined:

The correlation of the entire average curve, the average curve of the day and the average curve of the night in a comparison between six weeks and three months after implantation;

the cross correlation coefficients of these three curves between various patients at the points of time specified;

the cross correlation of the day average and night average of each patient six weeks and three months after implantation;

the peak-to-peak amplitude (difference between the maximum and minimum) of the overall average curve, the average curve of the day and the average curve of the night; and the course and the average of the standard deviation of the average curves.

Figure 1:
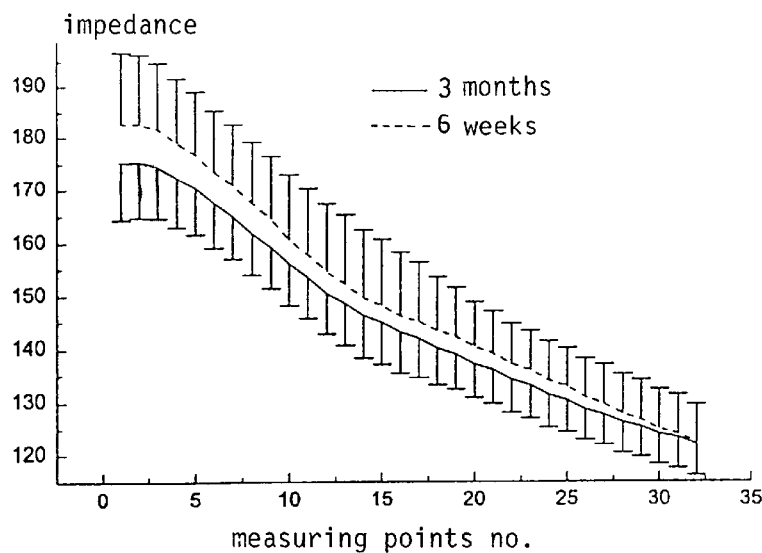
FIG. 1 is a diagram of the averaged impedance signal course with an averaging time over the entire course of the day.
Figure 2:
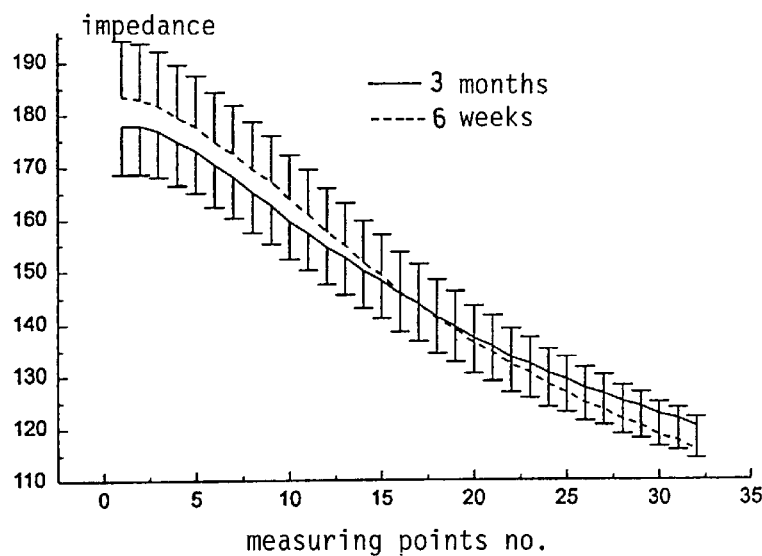
FIG. 2 is a diagram analogous to FIG. 1 with an averaging time over only the hours of the day.
Figure 3:
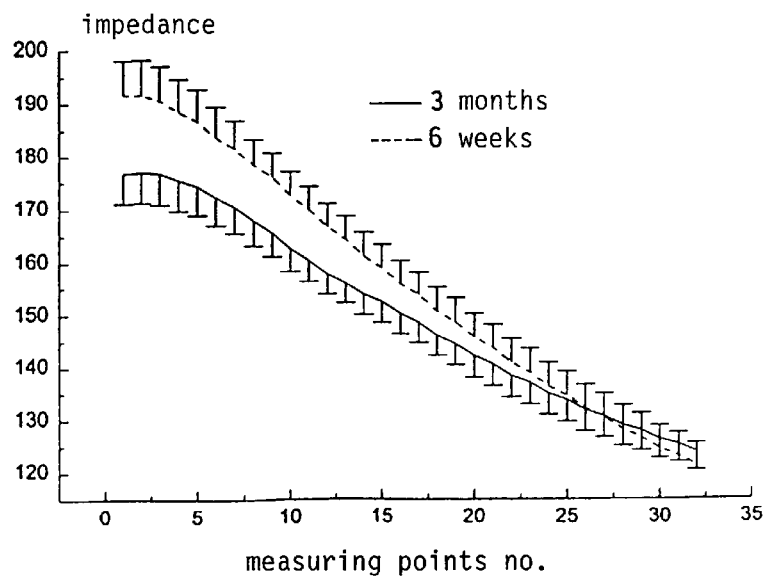
FIG. 3 is a diagram analogous to FIGS. 1 and 2 with an averaging time over only the hours of the night.

FIG. 1 reflects a typical morphologic signal course of the cardiac impedance during a semi-cycle of the heart. In this diagram—as well as in FIGS. 2 and 3—the 32 measuring points for dissolution of the morphologic signal course are plotted on the x axis. The intracardiac impedance is plotted in arbitrary units on the y axis. The dashed line in the diagrams represents the morphologic signal course during the measurements six weeks after implantation, the solid line three months after implantation. The vertical beams reflect the standard deviation of these mean values. The resulting morphologies after six weeks and three months of the typical patient represented in FIGS. 1 to 3 give rise to the following statements:

Between six weeks and three months, the amplitude of the averaged impedance curve is damped i.e., the difference between the maximum and minimum within the measuring window is decreased.

The damping effect on the overall average curve mainly seems to result from the damping of the night curve.

The qualitative morphology is comparatively stable during the time of the after-care examination.

The qualitative morphology depends to a minor extent on the day/night difference.

Computing various correlation coefficients on the basis of the measurements will give the following results.

The linear correlation coefficient of each average curve compared with itself even at points of time six weeks and three months is a direct parameter for the detection of changes in the morphology. As seen from the tables according to FIGS. 4 and 5, the correlations between the overall averages at points of time six weeks and three months deviate a bit more strongly from 1.0 only for patients 5, 6 and 7 than for the rest of the patients. Also the separate average curves for the day and the night show a good correlation between six weeks and three months. In this regard, the average curves have an extreme stability as far as long-term modifications are concerned. Comparing the respective curves of various patients should result in a greater variability than in the case of comparisons within a single patient, which corresponds to a lower correlation coefficient. This effect may be time dependent, as becomes apparent from the cross correlation coefficient in comparison to the tables according to FIGS. 4 and 5. In the case of the cross correlation coefficients three months after implantation (FIG. 5), the minimal correlation coefficient is indeed 0.64, whereas this minimal coefficient still amounts to 0.92 six weeks after implantation. This signals that morphologies which are rather comparable for various patients initially after implantation will drift apart in the course of time.

Owing to the high correlation coefficients of the day as well as of the night average—as they become apparent from FIGS. 4 and 5—these measurement curves can be used as a basis for evaluations and adjustments of operating parameters in cardiac pacemakers in spite of the high standard deviation, which is put into practice by the operating method according to the invention. For instance a change from day to night (or vice versa) in the sense of the operating method according to the invention can be determined on the basis of the morphologic signal courses of the intracardiac impedance by continuous computation of the stored parameter data in the form of the measuring points indicated for instance in FIGS. 1 to 3. To this end, the correlation coefficients are continuously computed during a certain interval which progresses continuously along with the measuring time. If we are in the day or night cycle, this continuous computation steadily determines autocorrelation coefficients which are close to 1.0 according to the tables of FIGS. 4 and 5. As soon as the evaluation interval runs into a change from day to night (or vice versa), the autocorrelation coefficient decreases, owing to the change of the morphologic signal course (see difference between the course of the curves in FIGS. 2 and 3); it passes through a minimum, and again approaches the high values close to 1.0 when the change from day to night has run out of the evaluation interval. This passage through a minimum is determined by a comparison of the correlation coefficients with a reference correlation coefficient, which has been determined by clinical tests or continuously from preceding measurements and which is stored in the heart pacemaker, transgression of a defined deviation of these two values from each other indicating the presence of the significant event in the form a change from day to night and being able to be translated by the pacemaker into corresponding changes in the pacemaker parameters (e.g. change of stimulus thresholds, of the rate etc.).

The evaluation, mentioned above, of the morphological signal courses of the intracardiac impedance may also be used for recognition of pathologic conditions of the heart or as an early warning thereof. For example so-called extra-systoles i.e., ventricular contractions of the heart in addition to the regular heart rate, or ischaemic phases will lead to signal courses of a very low correlation to that of healthy patients. In this regard, correlation coefficients such as the standard deviation in the case of the day average or night average signal, can be compared with those of healthy patients. If the standard deviation is high due to high fluctuations of the morphologic signal course, a transgression of a defined deviation from a reference correlation coefficient for the standard deviation is recognized by the evaluation program of the pacemaker and can be detected in a significant way as presence of a possibly pathologic condition of the heart. Correspondingly, the implantable cardiologic device may set a warning signal which is telemetrically transferable for instance to a monitoring center, or it may change its operating program. The monitoring center may take corresponding measures for patient care.

Figure 6:
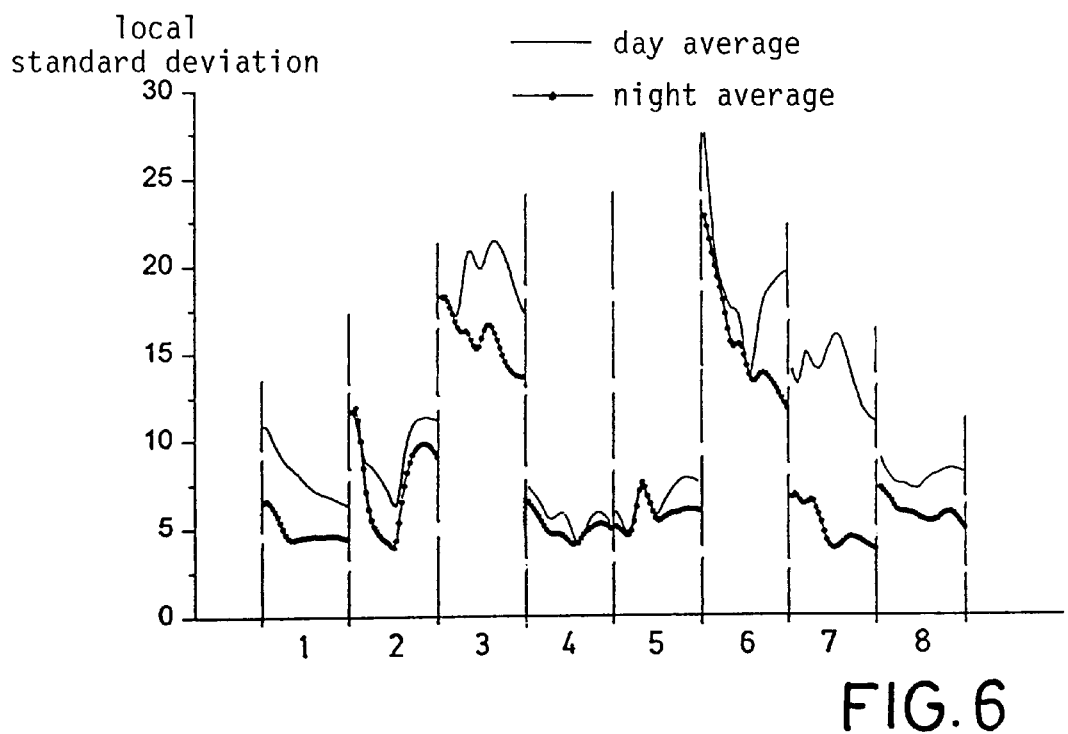
FIGS. 6 and 7 are diagrams of the course of the standard deviation of the mean value curves of the day and the night of various patients, six weeks or three months, respectively, after implantation of the pacemaker.
Figure 7:
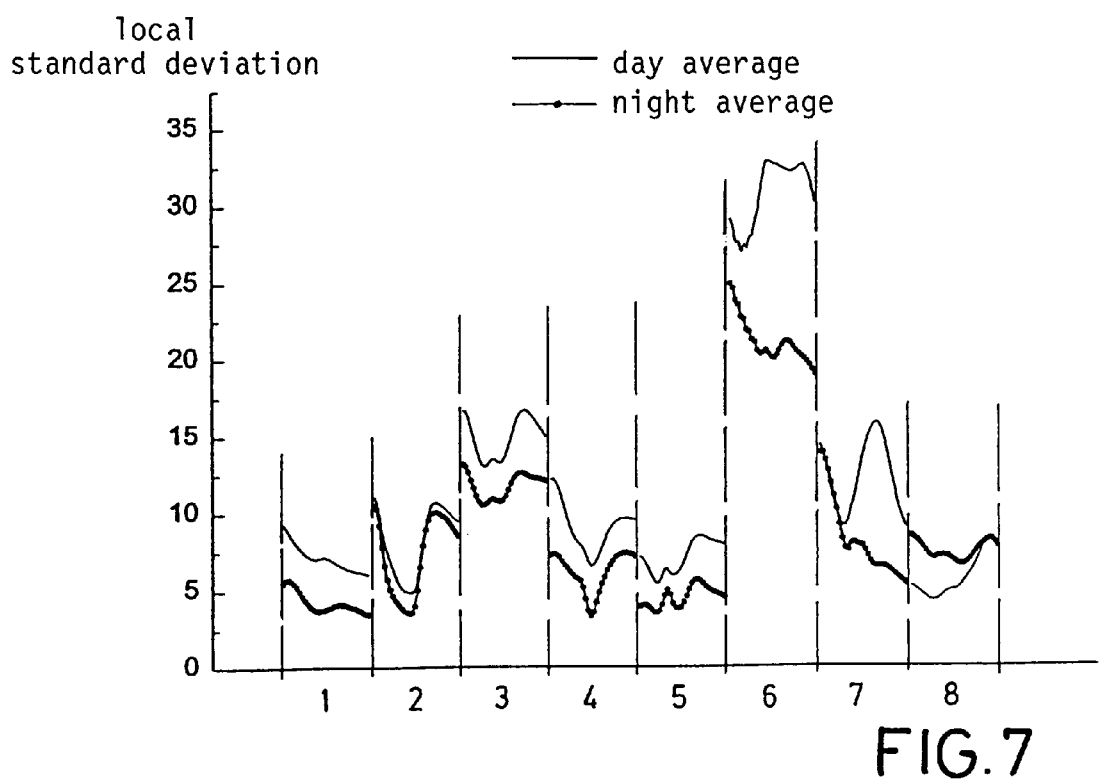

In FIGS. 6 and 7, the standard deviations of the day and night average are plotted as arbitrary units for the various patients (Nos. 1 to 8 on the x axis). The curve reflects the course of standard deviation during the measurement window of time for each patient. As seen in FIG. 6, the standard deviation is significantly increased in the case of the patients no. 3 and 6, which points to problems. FIG. 7 shows that, during the period of six weeks after implantation (FIG. 6) up to three months after implantation (FIG. 7) of the cardiac pacemaker, the standard deviation has clearly decreased for the patient no. 3, which suggests that this patient is approaching "normal conditions".

Figure 8:
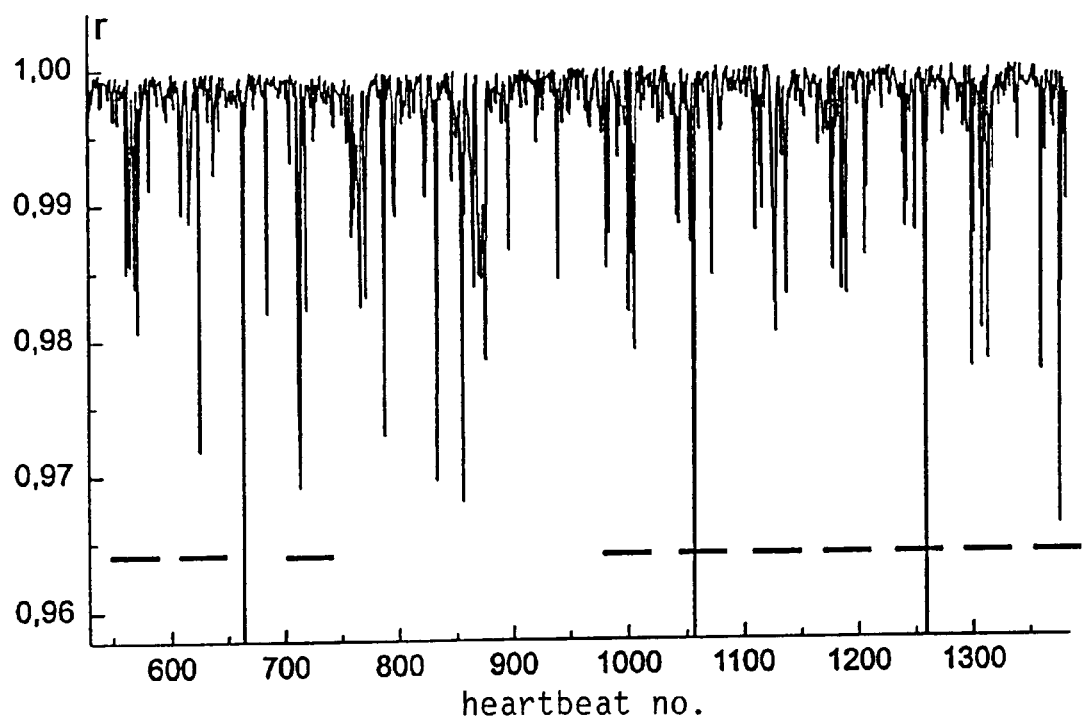
FIG. 8 is a diagram illustrating a cutout of the chronological course of the linear correlation coefficient of a patient, six weeks after implantation of the pacemaker.

Finally, also periodically recurring influences on cardiac activity at low frequencies for instance in the range of 0.1 Hz or 0.25 Hz may be detected alternatively on the basis of the measured and stored parameter data. A cardiac pacemaker equipped with a corresponding operating method will detect the chronological course of the deviation of the individual signal courses from an averaged mean signal course or from a given reference signal course and analyze it by means of spectral analysis such as a fast Fourier transformation so that regularly recurring deviations within the signal courses at low repetition frequencies are detectable. In annexed FIG. 8, the correlation coefficient r on the y axis is plotted in dependence on time (here represented by successive heartbeats of the numbers running from below 600 to more than 1300) on the x axis. As seen from this diagram, drops of the correlation coefficient occur at regular intervals, although the absolute change of the correlation coefficient is only in the range of approximately 0.02. The curve pattern seen in FIG. 8 is strongly similar to the behavior of the respiration rate under the influence of the so-called Cheyne-Stokes syndrome. With this disease, respiration takes place at a certain base frequency, it is however reduced by a constant range at regular intervals. In this regard, owing to measurement and evaluation of the signal morphology of the intracardiac impedance, corresponding findings may be obtained, and signaled in the form of a warning signal, by the aid of the cardiac pacemaker, even by way of extra-cardiac—in particular pulmonary—influences and symptoms.

Similar influences as in FIG. 5 may occur for instance at a frequency of 0.1 Hz. They are connected with vagal and sympathetic nerve activity in combination with blood pressure. Increased vagal influence, to be expected from fluctuations of the correlation coefficient at a frequency of 0.1 Hz, would suggest that the heart rate is superelevated for the prevailing physiological circumstances. This might be a hint to ischaemic phases or unsuitable adjustments of the cardiac pacemaker. A correspondingly evaluated signal may be used as a reference for the pacemaker adjustments to be optimized automatically by modification of the operating program. Not least it is also possible to determine rejection-diagnostic evaluation results after organ/heart transplantations.

What is claimed is:

1. An operating method for an implantable cardiologic device, for detection of a significant event or condition to which a patient is subject, comprising:

measuring intracardiac impedance;

detecting a morphologic signal course of the intracardiac impedance, based on at least one morphologically representative parameter of the signal course;

continuously storing said parameter from a defined measuring period;

computing a correlation coefficient for said stored parameter; and comparing the correlation coefficient with a reference correlation coefficient, with transgression of a defined deviation of the correlation coefficient from the reference correlation coefficient indicating a presence of at least one of said significant event and condition.

2. A method according to claim 1, comprising recording a multiplicity of measuring points as parameter data during a cardiac period for detecting the morphologic signal course of the impedance.

3. A method according to claim 2, comprising determining an autocorrelation coefficient of data of the stored parameter as a correlation coefficient.

4. A method according to claim 2, comprising determining a square or standard deviation of the data of the stored parameter as a correlation coefficient.

5. A method according to claim 1, comprising recording two parameter data which reflect a peak-to-peak amplitude of the morphologic signal course.

6. A method according to claim 1, comprising continuously computing and comparing the correlation coefficients to the reference correlation coefficients.

7. A method according to claim 1, comprising continuously storing the correlation coefficients computed during a certain interval for evaluation purposes.

8. A method according to claim 1, comprises evaluating the stored correlation coefficients such that a passage through a minimum is recognized as a change from day to night or from night to day; and adjusting an operating program of the implantable cardiologic device corresponding to the recognized day-night-change.

9. A method according to claim 1, comprising evaluating the stored correlation coefficients such that transgression of a defined deviation from reference correlation coefficients is recognized in a significant way as a presence of a possibly pathologic condition of the heart; and wherein the implantable cardiologic device sets a corresponding warning signal.

10. A method according to claim 1, comprising adjusting the reference correlation coefficients in dependence on a duration of implantation of the implantable cardiologic device.

11. A method according to claim 1, comprising detecting and analyzing on the basis of the parameter data for the intracardiac impedance, the chronological course of the deviation of the individual signal courses thereof from one of an averaged mean signal course, a given reference signal course, and each other, by spectral analysis detecting regularly recurring deviations of frequencies that are coupled with physiological functions of the body.

12. A method according to claim 1, comprising selecting between various evaluation methods and parameters.

13. A method according to claim 12, comprising selecting between various evaluation methods and parameters automatically in dependence on the preceding evaluation result.

14. A method according to claim 12, comprising selecting between various evaluation methods and parameters automatically by presetting an operating program of the implantable device.

* * * * *